(12) United States Patent
Innocenti et al.

(10) Patent No.: US 12,390,204 B2
(45) Date of Patent: Aug. 19, 2025

(54) CARDIAC MASK DEVICE AND PROCESS FOR MAKING THE CARDIAC MASK

(71) Applicants: Bernardo Innocenti, Ixelles (BE); Carlo De Asmundis, Dworp (BE)

(72) Inventors: Bernardo Innocenti, Ixelles (BE); Carlo De Asmundis, Dworp (BE)

( * ) Notice: Subject to any disclaimer, the term of this patent is extended or adjusted under 35 U.S.C. 154(b) by 404 days.

(21) Appl. No.: 17/937,049

(22) Filed: Sep. 30, 2022

(65) Prior Publication Data

US 2024/0108320 A1   Apr. 4, 2024

(30) Foreign Application Priority Data

Sep. 30, 2021   (IT) ........................ 102021000025157

(51) Int. Cl.
*A61B 5/00* (2006.01)
*A61B 17/00* (2006.01)
*A61N 1/362* (2006.01)
*A61B 18/00* (2006.01)

(52) U.S. Cl.
CPC ...... *A61B 17/00234* (2013.01); *A61N 1/3621* (2013.01); *A61B 2017/00243* (2013.01); *A61B 2017/00929* (2013.01); *A61B 2018/00577* (2013.01)

(58) Field of Classification Search
CPC .......... A61B 2018/00577; A61B 2018/00875; A61B 2018/00982; A61B 2090/0472; A61B 2090/0481; A61B 2090/049; A61B 90/04
See application file for complete search history.

(56) References Cited

U.S. PATENT DOCUMENTS

2006/0247610 A1 * 11/2006 Lanphere ............ A61L 27/3683
                                                                 606/21
2010/0305560 A1   12/2010 Peterson
2014/0022250 A1    1/2014 Mansi et al.

FOREIGN PATENT DOCUMENTS

WO        2018060304 A1    4/2018
WO     WO-2021163756 A1 *  8/2021 ......... A61B 17/0493

OTHER PUBLICATIONS

Search Report mailed May 18, 2022 for IT202100025157 filed Sep. 30, 2021, 8 pages.

* cited by examiner

*Primary Examiner* — Sana Sahand
(74) *Attorney, Agent, or Firm* — Vorys, Sater, Seymour and Pease LLP

(57) ABSTRACT

It is provided a cardiac mask configured for use in a cardiac ablation, including a ponent aperture in view of the at least one zone of interest identifying a portion of the heart undergoing cardiac ablation, made of an electrically insulating material and substantially counter-shaped to the heart so as to be rested on the heart during cardiac ablation.

17 Claims, 2 Drawing Sheets

CARDIAC MASK DEVICE AND PROCESS FOR MAKING THE CARDIAC MASK

FIELD OF THE INVENTION

It is an object of the present invention to provide a cardiac mask capable of identifying areas of diagnostic and therapeutic interest (in the field of cardiac electrophysiology?) suitably for cardiac ablation, and related device and making process of the type specified in the preamble of the independent claims.

BACKGROUND OF THE INVENTION

In particular, the mask is configured to, suitably in the context of cardiac electrophysiology, allow identification of areas of diagnostic and therapeutic interest.

The cardiac electrophysiology is the branch of medicine that deals with the interplay between electrophysiology (which studies the electrical phenomena associated with the functioning of living organisms) and cardiology (which studies the physiology and pathology of the heart); that is, cardiac electrophysiology studies and treats disorders associated with the electrical functioning of the heart. In particular, its aim is to diagnose and possibly treat abnormal electrical circuits within the heart that are responsible for arrhythmias.

Among the various treatments used by this branch, cardiac ablation, by interventional or surgical technique, is a therapeutic treatment reserved for people suffering from cardiac arrhythmias or other alteration of the heart's normal physiological rhythm.

The cardiac ablation is a minimally invasive medical procedure performed by a cardiologist specialised in electrophysiology. In one example, it involves the use of catheters, which are inserted into the body through a venous access, and from there led to the heart, where it will be operated.

The position of the catheter is very important and is performed via epicardial access (on the external surface of the heart tissue) through an 'open chest' approach, usually concomitant with cardiac bypass or heart valve replacement treatments, or thoracoscopically, which involves access into the thoracic space through laparoscopic procedures.

The ablation is done using devices that have electrodes (usually three) that record the heart's electrical activity so as to identify the area of the heart that is not functioning properly, and an ablator that destroys this aberrant tissue, thus eliminating the cause of the heart problem. Such device can be of different types: radiofrequency (radiofrequency cardiac ablation), laser (laser cardiac ablation), or low-temperature (cardiac cryoablation), or with high-intensity energy delivery at a specific frequency that, as it passes through the cardiomyocytes, causes a micro-perforation of the cell membranes, favouring apoptosis by the release of cytoplasm, called electroporation (electroporation ablation)

Although the cardiac ablation is considered a moderately invasive procedure, it has some major drawbacks.

In particular, ablation, in order to solve the problem, must be performed throughout the affected portion of the heart without, at the same time, damaging healthy portions of the heart. Therefore, this procedure is extremely dependent on the skill and experience of the cardiologist or surgeon who manipulates and handles the instrument.

This is particularly evident when one considers that the information available to the clinician is extremely limited. In ablations that require the surgeon's intervention, the heart is often placed in an inactive electrical condition supported by extracorporeal circulation, so the difficulty of identifying this area, which is visible due to its electrical properties, is evident, or in other conditions called beating heart where the abnormal electrical condition unfortunately lasts for only a few minutes and is therefore difficult to detect in real time. For this purpose, cardiac mapping tools are used to locate the areas of interest by creating images that can guide the surgeon to find the areas following anatomical parameters; this requires personal abstraction skills because the images cannot be correlated in real time with the heart during surgery.

This difficulty is further exacerbated by the pulsations/beats of the heart that continuously vary the profile of the heart itself.

SUMMARY OF THE INVENTION

In this situation, the technical task underlying the present invention is to devise a cardiac mask and related device and making process capable of substantially obviating at least part of the aforementioned drawbacks.

In the context of said technical task, it is an important aim of the invention to obtain a cardiac mask that allows cardiac ablation to be performed safely with objective parameters that are reproducible between operators and between patients in order to avoid empirical approaches that may damage areas not involved in the disease and independently of the surgeon's experience.

Another important aim of the invention is to realise a device and making process which enable a cardiac mask to be obtained easily and inexpensively.

The specified technical task and purposes are achieved by a cardiac mask and related device and making process as claimed in the annexed independent claims. Examples of preferred embodiments are described in the dependent claims.

BRIEF DESCRIPTION OF THE DRAWINGS

The features and advantages of the invention are hereinafter clarified by the detailed description of preferred embodiments of the invention, with reference to the appended drawings, in which:

the FIG. 1 illustrates a cardiac mask according to the invention; and the FIG. 2 shows an embodiment device of the cardiac mask; and the FIG. 3 illustrates a rear view of the cardiac mask of FIG. 1 that labels thicknesses $t_1$ and $t_2$.

DETAILED DESCRIPTION OF THE PREFERRED EMBODIMENTS

Figure 1:
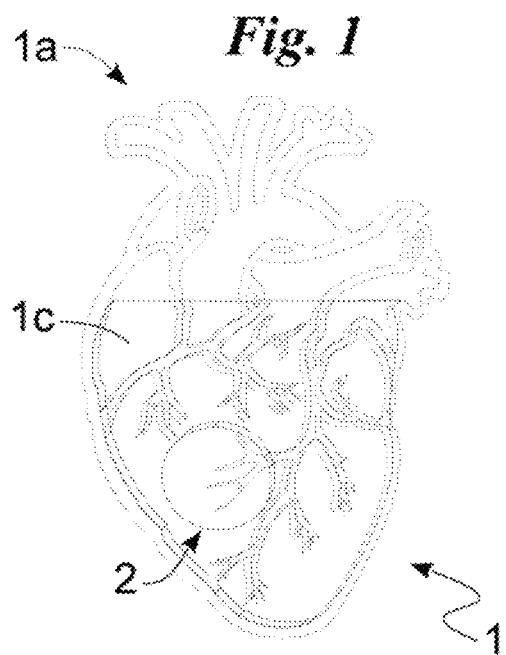
Figure 1:
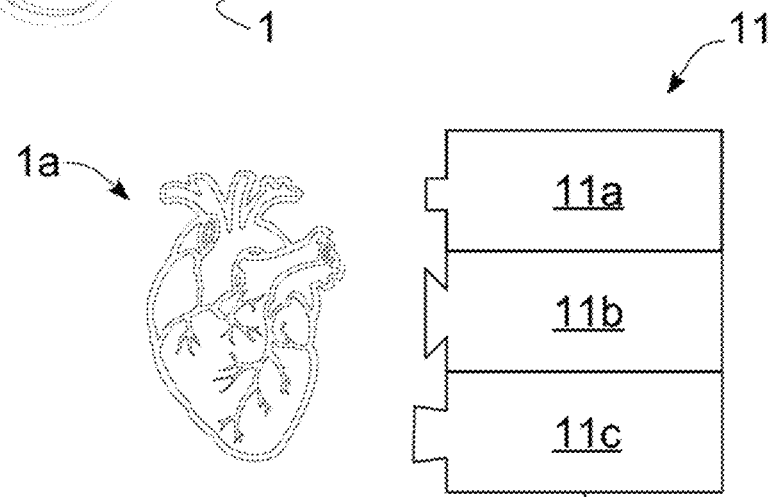

With reference to the Figures, the cardiac mask according to the invention is globally referred to by the number 1.

The cardiac mask 1 is configured to be used in a cardiac ablation and in particular for the destruction and thereby elimination from the heart 1a of one or more abnormal electrical pathways originating in cardiac arrhythmias or other alteration of the normal rhythm of the heart 1a.

The heart 1a may comprise at least one zone of interest and at least one zone of non-interest. The heart 1a may comprise one or more zones of interest each at least partially and in detail entirely surrounded by one or more zones of non-interest.

The zone of interest identifies the part of the heart 1a in which abnormal electrical pathways are present and which therefore needs to be treated by cardiac ablation; the zone of non-interest identifies the part of the heart 1a in which normal electrical pathways are present and which therefore does not give rise to any alteration in the normal rhythm of the heart 1a.

The cardiac mask 1 can be made of an electrically insulating material. In detail, the electrical conductivity of said material and thus of the mask 1 is substantially less than $10^{-5}$ S/m, in detail $10^{-10}$ S/m, in more detail $10^{-15}$ S/m and in more detail still $10^{-20}$ S/m.

The cardiac mask 1 can be made of a thermally insulating material. In detail, the thermal conductivity of said material and thus of the mask 1 is substantially less than 10 W/mK in detail 5 W/mK, more in detail 1 W/mK and more in detail still 0.5 W/mK. For example, it is substantially equal to 0.20 W/mK.

Preferably, the cardiac mask 1 can be made of an electrically and thermally insulating material.

The material of which the cardiac mask 1 is made can also be biocompatible.

The material may have a density, expressed in g/cm³, substantially between 0.5 and 5, more particularly between 0.5 and 2, more particularly between 1.0 and 1.5 and preferably between 1.17 and 1.18.

The material may have a module of elasticity, expressed KMPa, substantially between 0.5 and 5, in detail between 1 and 4, more in detail between 2 3 3.3.

The material may be low in water absorption. In detail, its absorption capacity may be less than 5% and in detail 2%. It can be between 1.0 and 1.5. Preferably the material for making the mask 1 is in a polymer material appropriately for rapid prototyping.

An example of a possible material is an acrylic polymer such as MED625FLX™.

The cardiac mask 1 can be configured to be placed over the heart 1a during cardiac ablation and in particular in the vicinity of one or more areas of the heart 1a where one or more abnormal electrical pathways are located.

The cardiac mask 1 (FIG. 1) comprises, for each zone of interest, an aperture 2 (also termed herein as an opening) configured substantially counter-shaped to said zone of interest leaving it in view. It is so configured as not to overlap and thus leave in view the one or more portions of the heart 1a being subjected to cardiac ablation.

The mask 1 is configured to overlap and in detail rest on at least one zone of non-interest (at least part of the portion of the heart 1a not subject to cardiac ablation) thereby concealing it from view. It is therefore configured to overlap and in detail rest on at least part of the portion of the heart 1a not subject to cardiac ablation.

It is pointed out that the opening 2 is at least partially and preferably totally delimited by the cardiac mask 1.

The cardiac mask 1 may have a thickness of substantially less than 1.5 and in detail 1 cm between a first face 1b proximal and facing the heart 1a and a second face 1c distal from the heart 1a and facing away from the heart 1a. Preferably, the mask 1 has a non-constant thickness and in detail maximum near/corresponding to the zone of interest and thus the aperture 2 and suitably a minimum thickness distal from the zone of interest and thus the aperture 2. The maximum thickness may be substantially between 150% and 250% and in detail substantially 200% of the minimum thickness (e.g. the maximum thickness may be 0.6 cm and the minimum thickness 0.3 cm).

The cardiac mask 1 defines the first face 1b proximal and facing the heart 1a and the second face 1c distal from the heart 1a and facing away from the heart 1a.

The first face 1b can be configured to rest on the area of no interest. It may be nearly counter-shaped to part of the heart 1a and in detail to the at least one zone of non-interest so as to rest and/or adhere substantially in perfect motion only to said zone of non-interest.

The second face 1c is configured to be in view during the performance of cardiac ablation.

Figure 2:
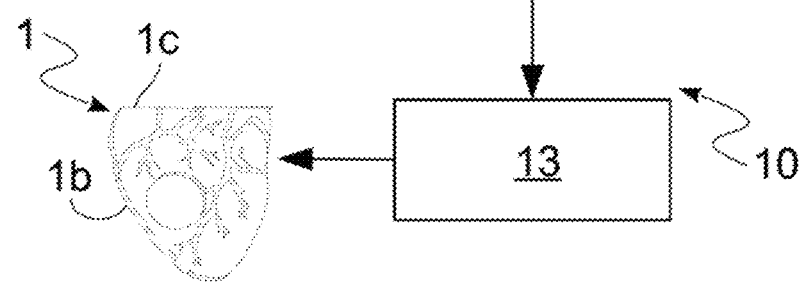
Figure 3:
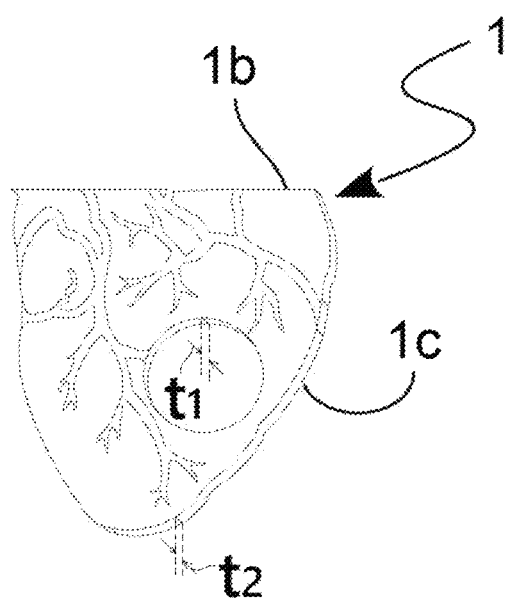

The invention comprises a novel embodiment device 10 (FIG. 2) for making the cardiac mask 1 described above.

The embodiment device 10 may comprise a heart acquisition organ 11 (also termed herein acquisition device or acquisition system) configured to perform a three-dimensional electro-anatomical map defining a three-dimensional representation of the electrical pathways of the heart 1a and thus of the electrical current moving in said heart 1a during a heartbeat.

The acquisition organ 11 may comprise a first system 11a configured to perform a three-dimensional acquisition of the heart 1a suitably defining the three-dimensional development of the heart 1a.

The first system 11a may comprise appropriately axial computed tomography (computed tomography CT). Alternatively, the first system 11a may comprise magnetic resonance imaging (MRI).

The acquisition system 11 may comprise a second system 11b configured to perform an electrical acquisition of the heart 1a, i.e. a two-dimensional electro-anatomical map identifying a chromatic (colour or greyscale) representation of the electrical pathways of the heart 1a.

The second system 11b may comprise a known cardiac electrophysiology device.

The acquisition device 11 may comprise a third system 11c configured to define the three-dimensional electro-anatomical map of the heart 1a as a function of the three-dimensional and electrical acquisitions.

The third system 11c is configured to make the three-dimensional electro-anatomical map by superimposing the electrical acquisition on the three-dimensional acquisition appropriately by matching the edges of the three-dimensional acquisition to the edges of the two-dimensional map.

The three-dimensional electro-anatomic map thus identifies an image whose three-dimensional development is defined, in detail exclusively, by the three-dimensional acquisition and whose colorimetric appearance is given, in detail exclusively, by the electrical acquisition.

The third system 11c may be a computer available in data connection with the first and second systems.

The embodiment device 10 may comprise a localisation device 12 (also termed herein localising organ) configured to detect and locate in the three-dimensional electro-anatomical map one or more zones of interest and then one or more zones of non-interest.

In detail, if the representation is substantially homogeneous, the organ identifies in the three-dimensional electro-anatomical map (i.e., in the heart 1a) the absence of present abnormal electrical pathways (i.e., zone of interest). Alternatively, if the representation is not homogeneous and shows one or more graphic alterations, the localising organ identifies and localises in the three-dimensional electro-anatomical map (i.e. in the heart 1a) the presence of one or more anomalous electrical pathways (i.e. zone of interest).

In the three-dimensional electro-anatomical map, the localisation organ 12 identifies and localises a zone of interest if there is a graphic alteration in it with colorimetric values within a predefined alarm range. For example, in the case of greyscale representation the alarm range, defined in accordance with the HSB scale, defines an area of interest for values of H substantially less than 50°, of S substantially less than 50% and of B substantially at least equal to 60%; and preferably for values of H substantially less than 20°, of S substantially less than 20% and of B substantially at least equal to 75%; while in the case of colour representation and in accordance with the HSB scale, the alarm range defines a zone of interest for values of H substantially less than 120°, of S substantially at least equal to 75% and of B substantially at least equal to 60%, in detail for values of H substantially less than 80, of S substantially at least equal to 80% and of B substantially at least equal to 90%.

Alternatively, the localisation organ 12 identifies and locates an area of interest as a graphic alteration with distinct colorimetric values from an adjacent area of at least a threshold colorimetric value. The threshold colorimetric value can be defined as a variation of at least 20% and in detail 30% of at least one and to be precise at least two values of the HSB scale.

The localisation organ 12 may comprise said alarm range and/or said threshold colorimetric value.

The localisation organ 12 may be a computer available in data connection with the third system and thus with the acquisition organ.

In summary, the localisation organ 12 defines a compound image given by the three-dimensional electro-anatomical map showing the at least one zone of no interest and preferably one or more zones of interest. The compound image then represents the mould against which the cardiac mask 1 is realised.

The embodiment device 10 may comprise a modelling organ 13 configured to model and thus make a cardiac mask 1 according to the three-dimensional electro-anatomical map and in particular of said compound image.

The modelling organ 13 is configured to make the mask 1 from electrically and/or thermally insulating material.

It is configured to make a cardiac mask 1 presenting a counter-shaped aperture 2 at the at least one area of interest identified by the localisation organ. In particular, it is configured to make a cardiac mask 1 nearly counter-shaped to the at least one zone of non-interest surrounding at least partially and preferably totally each of said at least one zone of interest.

Preferably the modelling organ 13 is a 3D printer.

The modelling organ 13 may be in data connection with the localisation organ 12.

The operation of the previously described embodiment device in structural terms defines a new making process of the cardiac mask 1.

The making process may comprise a phase of acquiring a three-dimensional electro-anatomical map defining a three-dimensional representation of the electrical pathways of the heart 1a.

The acquisition phase may comprise a first imaging sub-phase in which a three-dimensional acquisition of the heart 1a is performed.

The first imaging sub-phase may be a suitably axial computed tomography or magnetic resonance imaging.

The acquisition sub-phase may comprise a second imaging sub-phase in which an electrical acquisition of the heart 1a is performed resulting in a two-dimensional electro-anatomical map of the heart 1a defining a two-dimensional representation of the electrical pathways of the heart 1a.

The second imaging sub-phase may be cardiac electrophysiology.

The acquisition sub-phase may comprise an overlapping sub-phase in which said two-dimensional electro-anatomical map is superimposed on said three-dimensional acquisition producing the three-dimensional electro-anatomical map.

In this sub-phase, the superimposition can be performed by, for example, making the edges of the three-dimensional and electrical acquisitions coincide.

The acquisition phase can be performed automatically by the aforementioned acquisition organ.

The implementation procedure may comprise a localisation phase in which at least one zone of interest in the three-dimensional electro-anatomical map is identified and thus localised.

In the localisation phase, the at least one zone of interest is identified as the portion of the three-dimensional electro-anatomical map having a graphical alteration with colorimetric values included in the above-described alarm range or distinct from those of an adjacent zone by at least the threshold colorimetric value.

At the end of the localisation phase, a composite image may be produced from the three-dimensional electro-anatomical map showing at least one zone of no interest and appropriately the at least one zone of interest identified.

The localisation phase can be performed automatically by the aforementioned localisation organ. Alternatively, it can be performed by the operator.

The making process may comprise a modelling phase in which said cardiac mask 1 is realised according to said three-dimensional electro-anatomical map and in detail of said composite image.

In the modelling phase, a mask 1 is realised presenting a counter-shaped aperture 2 at each zone of interest. In particular, the cardiac mask 1 is made substantially counter-shaped to a portion of the three-dimensional electro-anatomical map comprising at least one zone of non-interest surrounding at least partially and in full detail each zone of interest.

The modelling phase is realised by 3D moulding appropriately of an electrically insulating material.

This phase can be performed automatically by said modelling body.

The use of the mask 1 defines a new cardiac ablation procedure.

The cardiac ablation procedure may comprise the above-described making process.

The cardiac ablation procedure may comprise an intervention procedure.

The intervention procedure may include opening the sternum so that the heart 1a is accessible; placing the cardiac mask 1 over the heart 1a; performing cardiac ablation; removing the mask 1 and then closing the intervention area.

The cardiac mask 1 and the related device and manufacturing process according to the invention achieve important advantages.

Indeed, the cardiac mask 1, by leaving in view only the portions of the heart 1a on which the ablation is to be performed, allows the procedure to be performed safely and precisely. This aspect is accentuated by the fact that the mask 1, being made of insulating material, does not spread the impulse used in ablation to other sectors of the heart 1a, thus avoiding damage to them.

An important advantage is that the adoption of the cardiac mask 1 makes it possible to considerably reduce the intervention time, making it safer for the patient and less costly. One advantage is that the mask 1 can be integrated into a known surgical procedure without substantially requiring modifications. It is therefore easily used by a surgeon.

Another important advantage is the fact that the device and making process are extremely quick and fast. This aspect makes it possible to make a patient-specific cardiac mask 1 and, above all, to make it immediately prior to surgery, optimising the success of cardiac ablation.

This aspect also ensures that the cardiac mask 1, which also has a first face 1b counter-shaped to the areas of no interest, remains perfectly in place during the procedure.

The invention is susceptible to variations within the scope of the inventive concept as defined by the claims. Within this scope, all details are substitutable by equivalent elements and the materials, shapes and dimensions may be any.

The invention claimed is:

1. A cardiac mask configured for use in a cardiac ablation of a heart;
   comprising at least an opening configured to leave in view and not overlap at least a zone of interest identifying a portion of the heart being ablated; and
   made of an electrically or thermally insulating material; and
   said mask defines a first face opposed to a second face, the first face suitable to be placed proximal and facing the heart and the second face suitable to be placed distal from the heart and facing away from the heart and configured to be in view during the cardiac ablation;
   said first face being counter-shaped to a zone of non-interest of said heart, surrounding at least partially the zone of interest and comprising at least a portion of said heart not subject to said cardiac ablation, so as to be configured to overlap and rest only on said zone of non-interest of said heart, thereby concealing said zone of non-interest from view during said cardiac ablation.

2. The cardiac mask according to claim 1, made of said electrically insulating material and wherein said electrically insulating material has an electrical conductivity less than 10-10 S/m.

3. The cardiac mask according to claim 2, made of said thermally insulating material and wherein said thermally insulating material has a thermal conductivity less than 1 W/mK.

4. The cardiac mask according to claim 1, made of said thermally insulating material and wherein said thermally insulating material has a thermal conductivity less than 1 W/mK.

5. The cardiac mask according to claim 1, said cardiac mask having a non-constant thickness and a maximum thickness corresponding to said opening and a minimum thickness distal from said opening.

6. The cardiac mask of claim 1, wherein said first face is counter-shaped to the zone of non-interest of said heart, wherein the zone of non-interest of said heart surrounds the zone of interest.

7. A device for making a cardiac mask,
   said cardiac mask configured for use in a cardiac ablation of a heart;
   said device comprising:
   an acquisition organ of said heart configured to perform a three-dimensional electro-anatomical map defining a three-dimensional representation of the electrical pathways of said heart;
   a localisation organ configured to identify in said three-dimensional electro-anatomical map at least one zone of interest in which abnormal electrical pathways of the heart are present;
   a modelling organ configured to make, according to said three-dimensional electro-anatomical map said cardiac mask,
   said cardiac mask made of an electrically or thermally insulating material,
   said cardiac mask defines a first face opposed to a second face, the first face suitable to be placed proximal and facing the heart and the second face suitable to be placed distal from the heart and facing away from the heart and configured to be in view during the cardiac ablation,
   said cardiac mask presenting an opening counter-shaped to said zone of interest by comprising the opening configured to leave in view and not overlap at least said zone of interest in which abnormal electrical pathways of the heart are present and identifying a portion of the heart being ablated, and
   said cardiac mask counter-shaped to at least a portion of said three-dimensional electro-anatomical map including at least a zone of non-interest surrounding at least partially said zone of interest, wherein said first face of said cardiac mask is counter-shaped to said zone of non-interest of said heart, surrounding at least partially said zone of interest and comprising at least a portion of said heart not subject to said cardiac ablation so as to be configured to overlap and rest only on said zone of non-interest of said heart, thereby concealing said zone of non-interest from view during said cardiac ablation.

8. The device of claim 7,
   wherein said cardiac mask is counter-shaped to at least the portion of said three-dimensional electro-anatomical map including at least the zone of non-interest, wherein the zone of non-interest surrounds the zone of interest, wherein the first face of the cardiac mask is counter-shaped to the zone of non-interest of the heart surrounding the zone of interest.

9. A process for making a cardiac mask,
   said cardiac mask configured for use in a cardiac ablation of a heart;
   said process comprising:
   an acquisition phase producing a three-dimensional electro-anatomical map defining a three-dimensional representation of the electrical pathways of said heart;
   an analysis phase wherein in said three-dimensional electro-anatomical map, at least one zone of interest is identified in which abnormal electrical pathways are present;
   a modelling phase in which, according to said three-dimensional electro-anatomical map,
   wherein said cardiac mask is made of an electrically insulating material;
   said cardiac mask defines a first face opposed to a second face, the first face suitable to be placed proximal and facing the heart and the second face suitable to be placed distal from the heart and facing away from the heart and configured to be in view during the cardiac ablation,
   said cardiac mask presenting an opening configured to provide to said zone of interest, wherein said cardiac mask comprises at least the opening configured to leave in view and not overlap at least said zone of interest identified in which abnormal electrical pathways are present and identifying a portion of the heart being ablated, and
   said cardiac mask being counter-shaped to at least a portion of said three-dimensional electro-anatomical map including at least a zone of non-interest surrounding at least partially said zone of interest, wherein said first face of said cardiac mask counter-shaped to said zone of non-interest of said heart surrounding at least partially said zone of interest and comprising at least a portion of said heart not subject to said cardiac ablation so as to be configured to overlap and rest only on said zone of non-interest of said heart, thereby concealing said zone of non-interest from view during said cardiac ablation.

10. The process for making according to claim 9, wherein in said modelling phase said cardiac mask is made by 3D moulding.

11. The process for making according to claim 9, wherein in said modelling phase said cardiac mask is made by 3D moulding of an electrically insulating material.

12. The process for making according to claim 9, wherein in said analysis phase said at least one zone of interest is identified if in said three-dimensional electro-anatomical map there is a graphical alteration with colorimetric values included in a predefined alarm range.

13. The process for making according to claim 12, wherein said three-dimensional electro-anatomical map is grayscale; and wherein in accordance with HSB scale said predefined alarm range defines said at least one zone of interest for values of H less than 20°, of S less than 20%, and of B at least 75%.

14. The process for making according to claim 12,
  wherein said three-dimensional electro-anatomical map is in colour; and
  wherein in accordance with HSB scale said predefined alarm range defines said at least one zone of interest for values of H less than 80, of S at least 80% and of B at least 90%.

15. The process of claim 9,
  wherein the cardiac mask is counter-shaped to at least the portion of the three-dimensional electro-anatomical map including at least the zone of non-interest, wherein the zone of non-interest surrounds the zone of interest, wherein the first face of the cardiac mask counter-shaped to the zone of non-interest of the heart surrounding the zone of interest and comprising at least the portion of the heart not subject to the cardiac ablation so as to be configured to overlap and rest only on the zone of non-interest of the heart, thereby concealing the zone of non-interest from view during the cardiac ablation.

16. A cardiac mask configured for use in a cardiac ablation of a heart;
  comprising at least an opening configured to leave in view and not overlap at least a zone of interest identifying a portion of the heart being ablated; and
  made of an electrically or thermally insulating material; and
  counter-shaped to a zone of non-interest of said heart, surrounding at least partially the zone of interest and comprising at least a portion of said heart not subject to said cardiac ablation so as to be configured to overlap and rest only on said zone of non-interest of said heart, thereby concealing said zone of non-interest from view during said cardiac ablation;
  said cardiac mask having a non-constant thickness and a maximum thickness corresponding to said opening and a minimum thickness distal from said opening.

17. The cardiac mask of claim 16, wherein said first face is counter-shaped to the zone of non-interest of said heart, wherein the zone of non-interest of said heart surrounds the zone of interest.

* * * * *